US011767839B2

(12) United States Patent
Powell

(10) Patent No.: US 11,767,839 B2
(45) Date of Patent: Sep. 26, 2023

(54) VACUUM PUMP

(71) Applicant: StakPac, LLC, Detroit, MI (US)

(72) Inventor: Patrick Kenneth Powell, Detroit, MI (US)

(73) Assignee: AG IP HOLDING, LLC, Okemos, MI (US)

( * ) Notice: Subject to any disclaimer, the term of this patent is extended or adjusted under 35 U.S.C. 154(b) by 0 days.

(21) Appl. No.: 17/587,147

(22) Filed: Jan. 28, 2022

(65) Prior Publication Data

US 2022/0154712 A1 May 19, 2022

Related U.S. Application Data

(63) Continuation of application No. 16/324,774, filed as application No. PCT/US2017/046460 on Aug. 11, 2017, now Pat. No. 11,236,742.
(Continued)

(51) Int. Cl.
*F04B 45/02* (2006.01)
*F04B 43/107* (2006.01)
(Continued)

(52) U.S. Cl.
CPC .......... *F04B 45/022* (2013.01); *A47C 27/081* (2013.01); *A47C 27/084* (2013.01);
(Continued)

(58) Field of Classification Search
CPC ........ F04B 45/02; F04B 43/107; F04B 43/08; F04B 43/10; F04B 43/1136; F04B 45/022;
(Continued)

(56) References Cited

U.S. PATENT DOCUMENTS 182,298 A 9/1876 Bangs
1,108,275 A 8/1914 Templin
(Continued)

FOREIGN PATENT DOCUMENTS

WO 2016065335 4/2016

OTHER PUBLICATIONS

International Search Report for International Application No. PCT/US2017/06460 completed Nov. 2, 2017.
(Continued)

*Primary Examiner* — Peter J Bertheaud
(74) *Attorney, Agent, or Firm* — Carlson, Gaskey & Olds, P.C.

(57) ABSTRACT

A vacuum pump includes a hollow container that has a vacuum port and internal chamber walls. The vacuum port opens to an exterior of the container and the chamber walls define chambers that are in fluid communication with the vacuum port. There are flexible bladders disposed in the chambers. The flexible bladders include vents that open through the container to the exterior. A plunger in the container includes arms that extend into the chambers such that each of the flexible bladders is situated between one of the arms and one of the chamber walls. The plunger is moveable between a home position and an upstroke position to compress and deflate the flexible bladders via the vents and thereby change the volume of the flexible bladders. The change in the volume draws a vacuum through the vacuum port.

14 Claims, 9 Drawing Sheets

Related U.S. Application Data

(60) Provisional application No. 62/475,266, filed on Mar. 23, 2017, provisional application No. 62/373,526, filed on Aug. 11, 2016, provisional application No. 62/373,513, filed on Aug. 11, 2016.

(51) Int. Cl.
  *F04B 33/00* (2006.01)
  *F04B 43/08* (2006.01)
  *F04B 43/10* (2006.01)
  *F04B 43/113* (2006.01)
  *A47C 27/08* (2006.01)

(52) U.S. Cl.
  CPC .............. *F04B 33/00* (2013.01); *F04B 43/08* (2013.01); *F04B 43/086* (2013.01); *F04B 43/10* (2013.01); *F04B 43/107* (2013.01); *F04B 43/1136* (2013.01); *F04B 45/02* (2013.01); *F04B 45/024* (2013.01)

(58) Field of Classification Search
  CPC ...... F04B 33/00; F04B 45/024; F04B 43/086; A47C 27/081; A47C 27/084
  See application file for complete search history.

(56) References Cited

U.S. PATENT DOCUMENTS

| | | |
|---|---|---|
| 1,780,336 A | 11/1930 | Canton |
| 2,578,265 A | 12/1951 | Bartlett |
| 2,735,369 A | 2/1956 | Turvey |
| 3,073,246 A | 1/1963 | Saunders et al. |
| 3,151,562 A | 10/1964 | Swartz |
| 4,634,430 A | 1/1987 | Polaschegg |
| 4,858,478 A | 8/1989 | Kush et al. |
| 4,947,491 A | 8/1990 | Parkinson et al. |
| 5,165,866 A | 11/1992 | Kato |
| 6,111,187 A | 8/2000 | Goyette |
| 6,348,043 B1 | 2/2002 | Hagen et al. |
| 9,518,577 B2 | 12/2016 | van Boeyen et al. |
| 11,236,742 B2 * | 2/2022 | Powell ............... F04B 43/10 |
| 2002/0188273 A1 | 12/2002 | Ko |
| 2009/0287190 A1 | 11/2009 | Shippert |
| 2014/0188061 A1 | 3/2014 | Locke et al. |
| 2014/0350511 A1 | 11/2014 | Carlisle et al. |
| 2016/0144093 A1 | 5/2016 | Demers et al. |
| 2019/0224414 A1 | 7/2019 | Schabbach et al. |

OTHER PUBLICATIONS

International Preliminary Report on Patentability for International Application No. PCT/US2017/046460 dated Feb. 12, 2019.

* cited by examiner

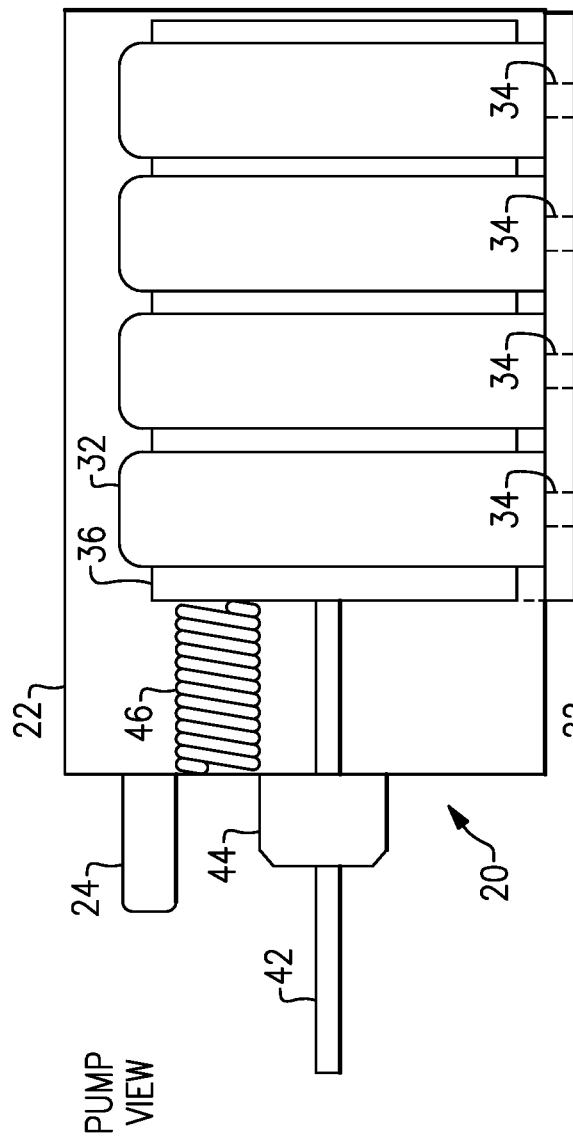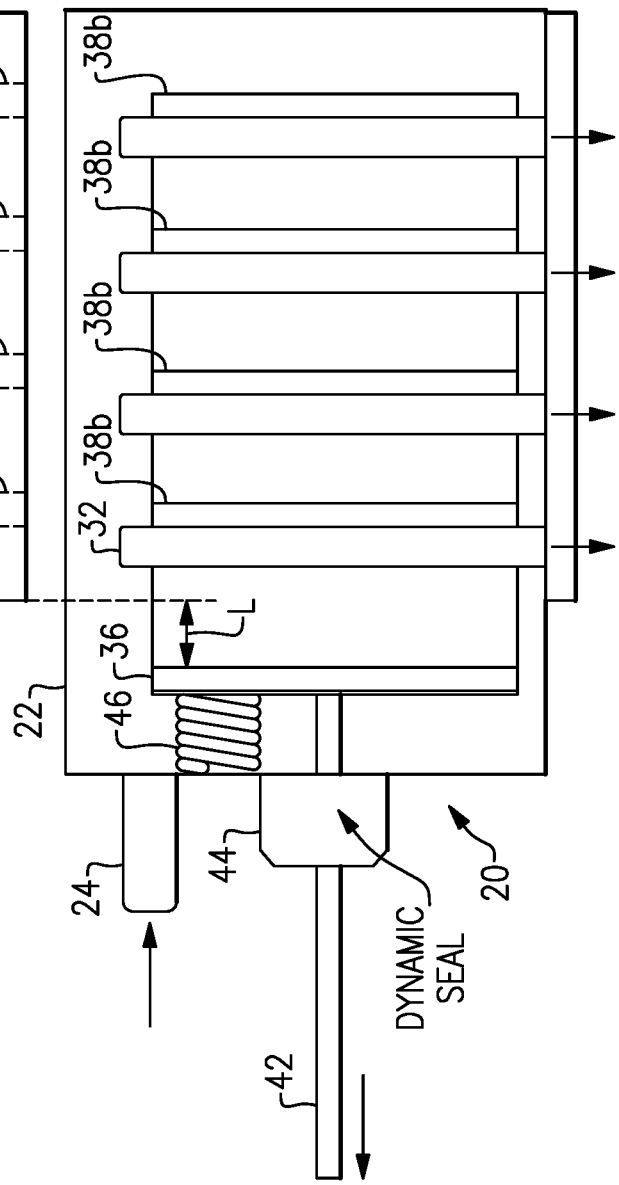

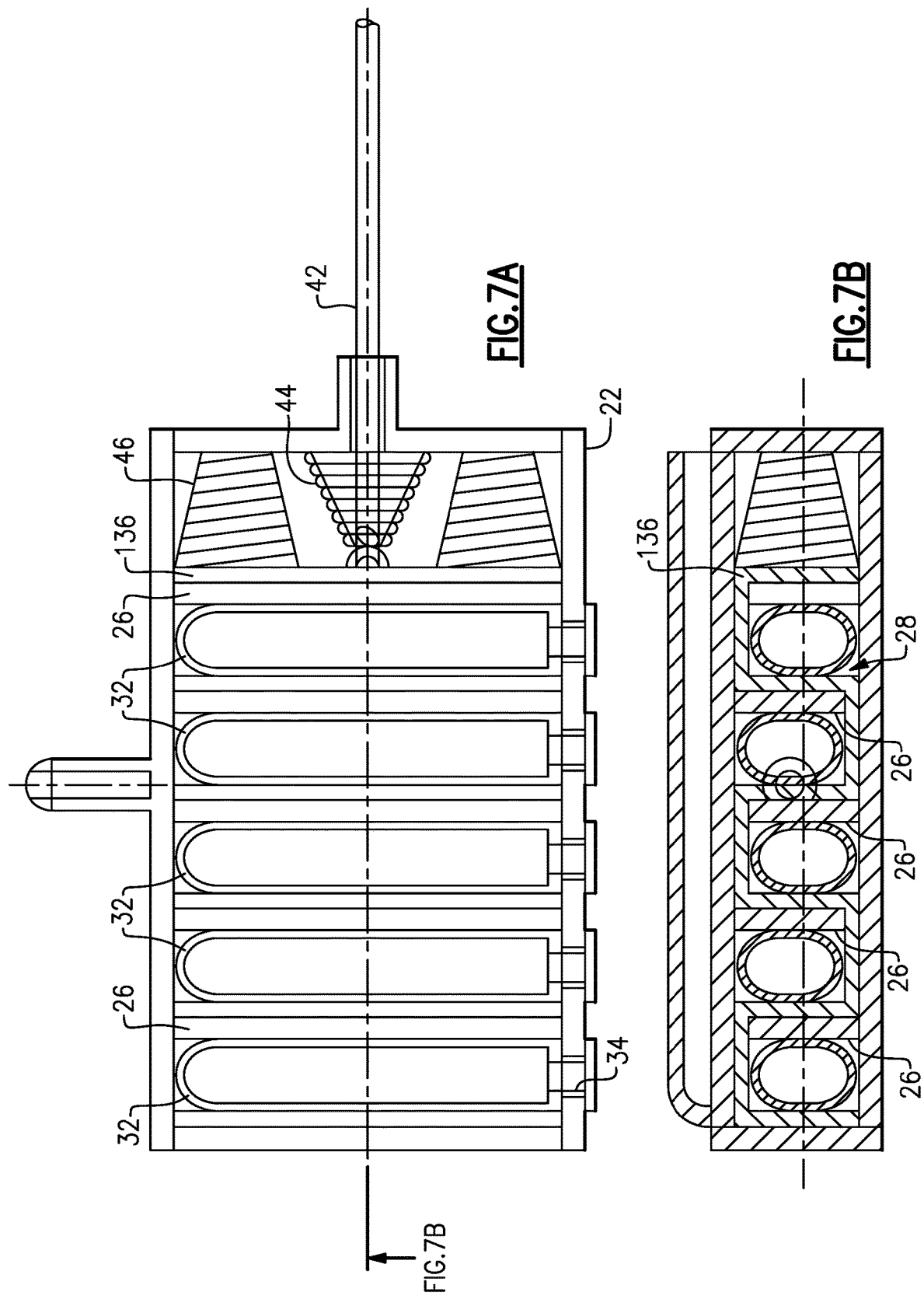

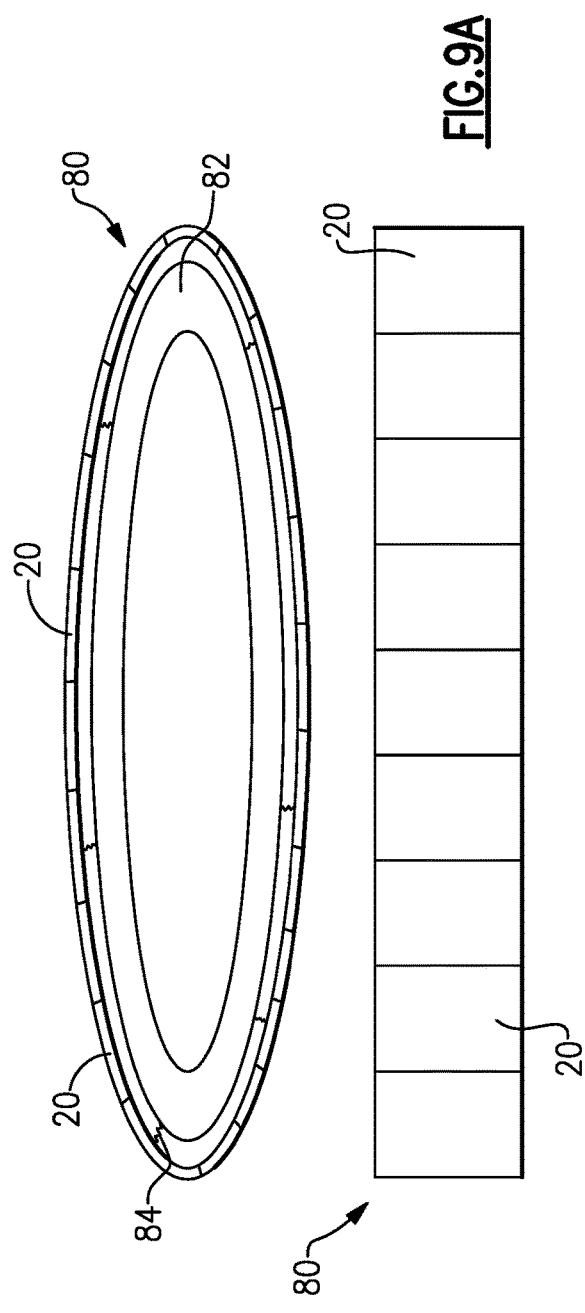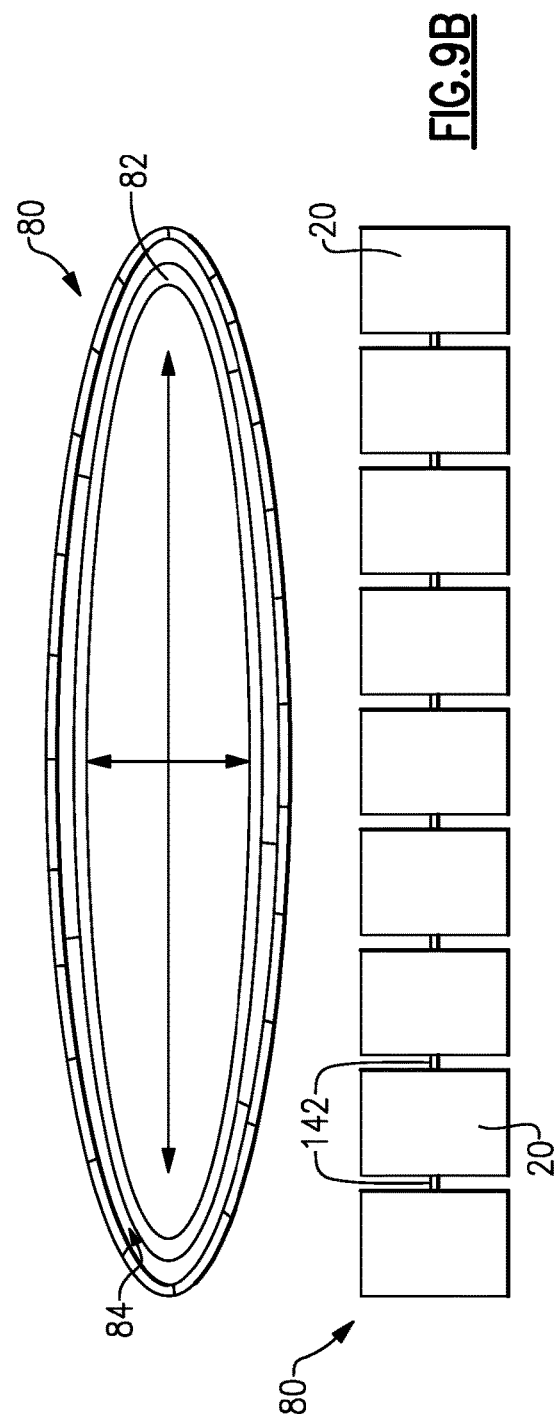

VACUUM PUMP

BACKGROUND

Pumps may be used for a variety of purposes, including biological purposes. For example, manual or battery-powered vacuum pump systems may be used for expressing and collecting milk. Vacuum pump systems may also be used for negative-pressure wound therapy to provide reduced pressure at a wound site to facilitate healing.

SUMMARY

A vacuum pump according to an example of the present disclosure includes a hollow container that has a vacuum port and internal chamber walls. The vacuum port opens to an exterior of the hollow container and internal chamber walls that define chambers that are in fluid communication with the vacuum port. Flexible bladders are disposed, respectively, in the chambers. Each of the flexible bladders has a vent that opens through the hollow container to the exterior of the hollow container. A plunger is disposed in the hollow container. The plunger has arms that, respectively, extend into the chambers such that each of the flexible bladders is situated between one of the arms and one of the internal chamber walls. The plunger is moveable between a home position and an upstroke position to compress and deflate the flexible bladders via the vents and thereby change the volume of the flexible bladders. The change in the volume draws a vacuum through the vacuum port.

A further embodiment of any of the foregoing embodiments includes a bias member operable to bias the plunger toward the home position and inflate the flexible bladders through the vents.

In a further embodiment of any of the foregoing embodiments, the flexible bladders are elongated tubes.

In a further embodiment of any of the foregoing embodiments, the plunger has a serpentine shape.

In a further embodiment of any of the foregoing embodiments, the arms of the plunger are parallel.

In a further embodiment of any of the foregoing embodiments, the chambers are elongated in a direction that is perpendicular to the direction of movement of the plunger.

A further embodiment of any of the foregoing embodiments includes a cord attached with the plunger and operable to move the plunger.

In a further embodiment of any of the foregoing embodiments, the hollow container defines an air plenum that fluidly connects the chambers with the vacuum port.

In a further embodiment of any of the foregoing embodiments, the flexible bladders are connected to each other as a single, monolithic piece.

In a further embodiment of any of the foregoing embodiments, the plunger defines a total stroke length, in units of millimeters, from the home position to the upstroke position such that upon movement from the home position to the upstroke position to draw the vacuum, in units of Torr, there is a ratio of the vacuum drawn to the total stroke length, the ratio (Torr/millimeters) being at least 20.

In a further embodiment of any of the foregoing embodiments, the flexible bladders are elongated tubes. The chambers are elongated in a direction that is perpendicular to the direction of movement of the plunger, and the hollow container defines an air plenum that fluidly connects the chambers with the vacuum port, and further includes a cord attached with the plunger operable to move the plunger and a bias member operable to bias the plunger toward the home position and inflate the flexible bladders through the vents.

A vacuum pump system according to an example of the present disclosure includes a plurality of vacuum pumps. Each vacuum pump has a hollow container that includes a vacuum port and internal chamber walls. The vacuum port opens to an exterior of the hollow container and internal chamber walls that define chambers that are in fluid communication with the vacuum port. Flexible bladders are disposed, respectively, in the chambers. Each of the flexible bladders has a vent that opens through the hollow container to the exterior of the hollow container, and a plunger is disposed in the hollow container. The plunger has arms that, respectively, extend into the chambers such that each of the flexible bladders is situated between one of the arms and one of the internal chamber walls. The plunger is moveable between a home position and an upstroke position to compress and deflate the flexible bladders via the vents and thereby change the volume of the flexible bladders. The change in the volume draws a vacuum through the vacuum port. The plungers of the vacuum pumps are linked for co-actuation.

In a further embodiment of any of the foregoing embodiments, the vacuum pumps are linked in a continuous loop.

In a further embodiment of any of the foregoing embodiments, each of the vacuum pumps further includes a bias member operable to bias the plunger toward the home position and inflate the flexible bladders through the vents.

In a further embodiment of any of the foregoing embodiments, the flexible bladders are elongated tubes and the chambers are elongated in a direction that is perpendicular to the direction of movement of the plunger.

In a further embodiment of any of the foregoing embodiments, each vacuum pump has at least three of the flexible bladders. The plunger defines a total stroke length, in units of millimeters, from the home position to the upstroke position such that upon movement from the home position to the upstroke position to draw the vacuum, in units of Torr, there is a ratio of the vacuum drawn to the total stroke length, the ratio (Torr/millimeters) being at least 20.

In a further embodiment of any of the foregoing embodiments, the vacuum pumps are linked by cords that are attached with the plungers.

In a further embodiment of any of the foregoing embodiments, the hollow container defines an air plenum that fluidly connects the chambers with the vacuum port.

A vacuum pump according to an example of the present disclosure includes a pump body that has an internal cavity and a vacuum port fluidly connecting the internal cavity with an exterior of the pump body. There is at least one bladder disposed in the internal cavity and vented to the exterior of the hollow container. A piston is disposed in the pump body and is moveable to compress and deflate the at least one bladder via the vent and thereby change the volume of the at least one bladder. The change in the volume draws a vacuum through the vacuum port.

A further embodiment of any of the foregoing embodiments includes an inflatable member located outside of the pump body and to which the pump body is secured.

BRIEF DESCRIPTION OF THE DRAWINGS

The various features and advantages of the present disclosure will become apparent to those skilled in the art from the following detailed description. The drawings that accompany the detailed description can be briefly described as follows.

FIGS. 6A and 6B schematically illustrate, respectively, a vacuum pump in a home position and in an upstroke position.

FIG. 7A illustrates another example of a vacuum pump.

FIG. 7B illustrates a sectioned view of the vacuum pump of FIG. 7A.

FIG. 9A illustrates a system with multiple vacuum pumps in a home position.

FIG. 9B illustrates a system with multiple vacuum pumps in an expanded position.

DETAILED DESCRIPTION

Figure 1:
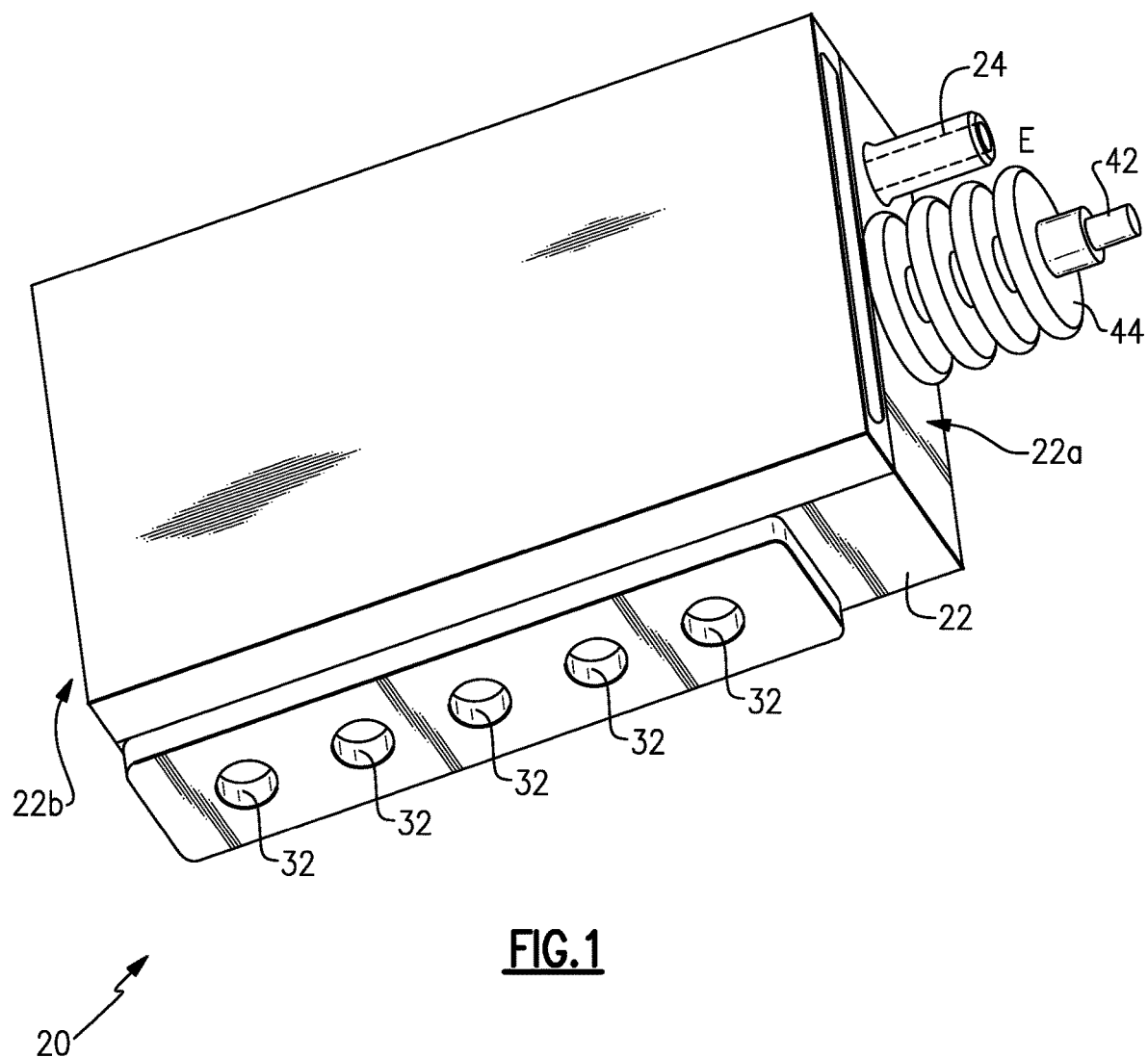
FIG. 1 illustrates an example vacuum pump.

FIG. 1 schematically illustrates a vacuum pump 20. A typical vacuum pump is bulky and therefore inappropriate for some potential end uses. In particular, "wearable" systems require not only functionality but also a reasonable level of comfort for the user. One such example is breast pumps and, more specifically, breast pumps that can be integrated into garments or other wearables. As will be described, the example vacuum pump herein is relatively compact and requires only low displacement to achieve a relatively high vacuum. As will be appreciated, although the examples may find use in wearables, other end use applications will also benefit from this disclosure.

Figure 2:
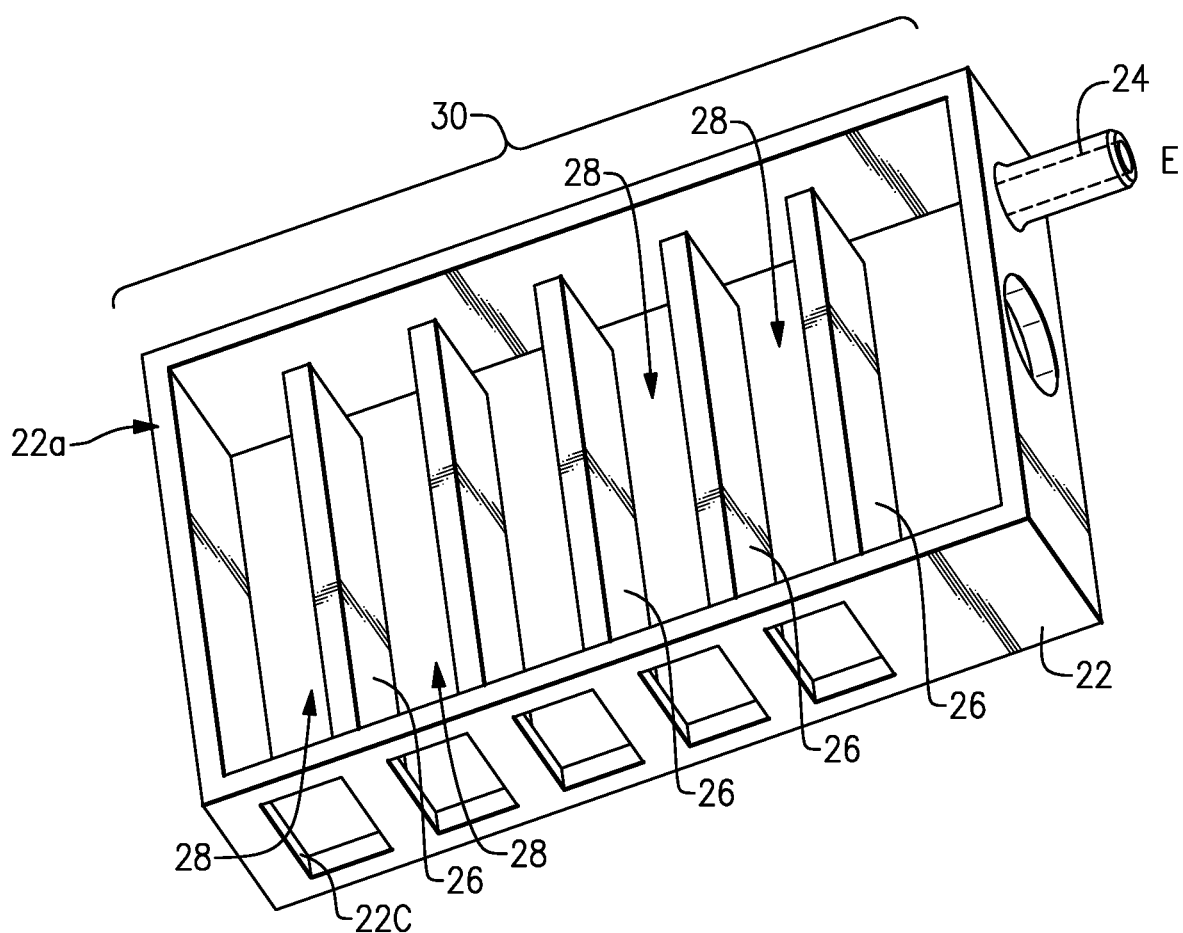
FIG. 2 illustrates an isolated view of a portion of a container of the vacuum pump.

The vacuum pump 20 includes a hollow container 22, which may also be referred to as a pump body, that has a vacuum port 24 that opens to an exterior (E) of the container 22. FIG. 2 shows an isolated view of a base portion 22a of the container 22, but as shown in FIG. 1 the container 22 in this example also has a cover portion 22b that is attached and sealed to the base portion 22a. The base and cover 22a/22b most typically are formed of plastic but are not limited thereto. As will be appreciated, although the container 22 in this example is a two piece configuration with the base and cover 22a/22b, the container 22 may be varied in shape and may be formed from more than two pieces or even from a single piece.

The container 22 defines internal chamber walls 26. The walls 26 generally subdivide the internal open cavity in the container 22. In this example, the walls 26 are spaced apart and are generally parallel to each other such that they define chambers 28 there between. The chambers 26 are in fluid communication with the vacuum port 24. In this example, the container 22 defines a common air plenum 30 that runs adjacent the chambers 26. The air plenum 30 fluidly connects the chambers 28 with the vacuum port 24. When the cover 22b is secured, each of the chambers 26 is enclosed except at one end which opens to the air plenum 30 and at an opposite end which has an opening 22c through a side of the base 22a.

Figure 3:
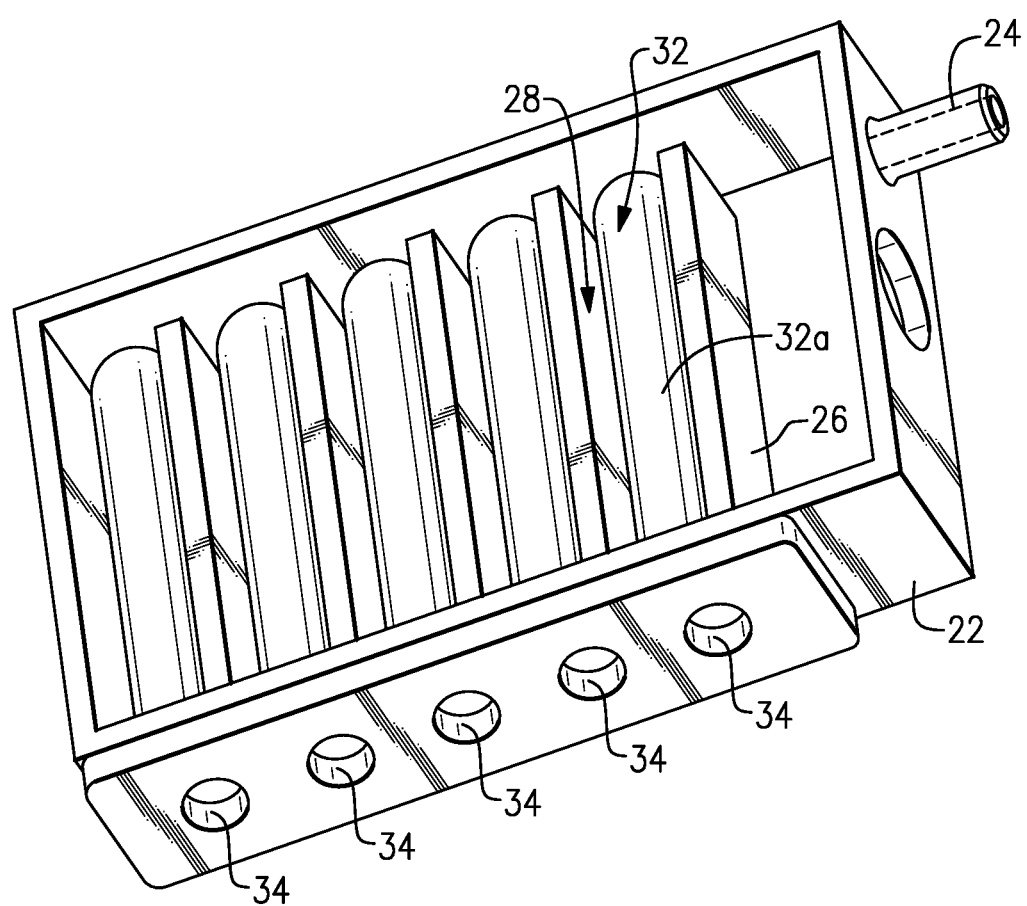
FIG. 3 illustrates an isolated view of a portion of the container of the vacuum pump and flexible bladders.

The vacuum pump 20 further includes flexible bladders 32 disposed, respectively, in the chambers 28. FIG. 3 shows an isolated view of the base 22a of the container 22 and the bladders 32. Each of the bladders 32 includes a vent 34 that extends through a corresponding one of openings 22c (FIG. 2) in the side of the container 22. The vents 34 open to the exterior of the container 22. In this example, each of the bladders 32 is or includes an elongated tube 32a. The tubes 32a are fully enclosed except for the vents 34 to the exterior and generally have a geometry that is complimentary to the geometry of the chambers 28. For example, each bladder 32 fits snuggly between the walls 26 such that there are no gaps between the bladder 32 and the walls 26. Also in this example, the bladders 32 are connected to each other as a single, monolithic piece. For instance, the piece is formed of elastomer and may be molded or otherwise formed as a single unitary component. Alternatively, each bladder 32 may be a separate piece formed from an elastomer.

Figure 4:
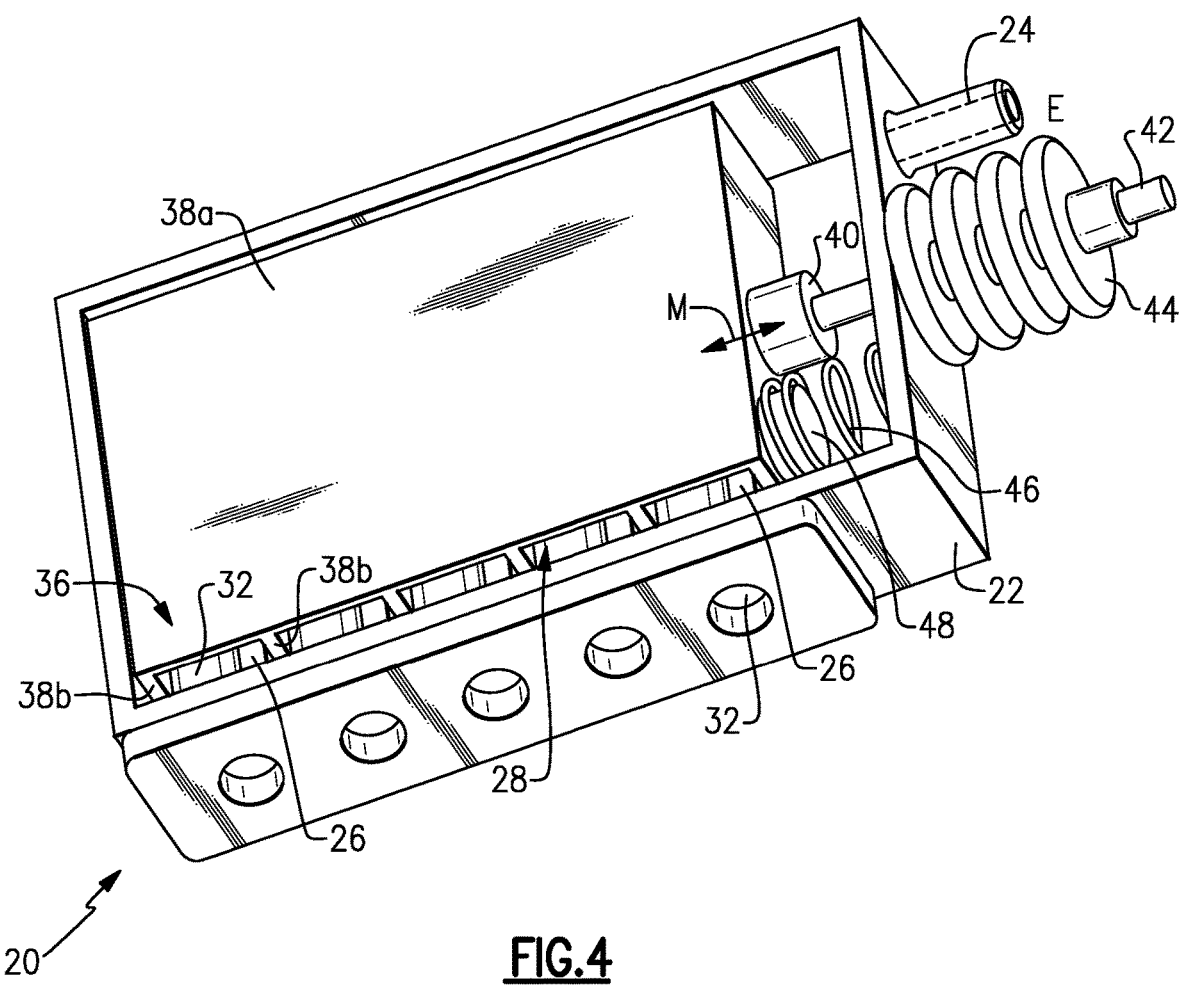
FIG. 4 illustrates an isolated view of a portion of the container of the vacuum pump, flexible bladders, and a plunger.
Figure 5:
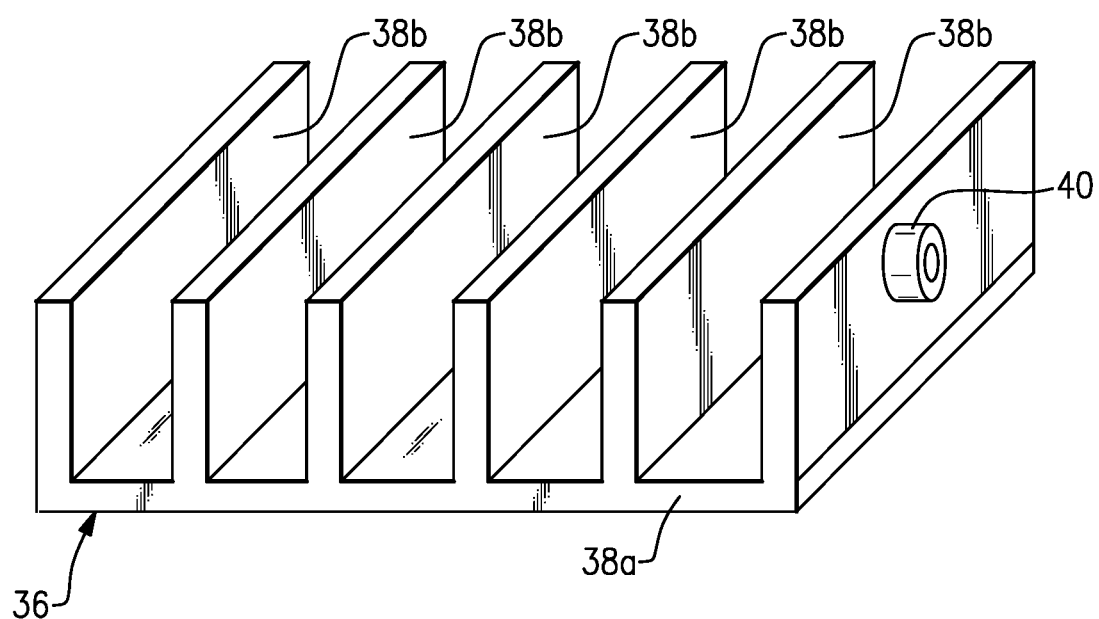
FIG. 5 illustrates an isolated view of the plunger.

FIG. 4 shows the vacuum pump 20 without the cover 22b. The vacuum pump 20 includes a plunger 36 disposed in the container 22. The plunger 36 is also shown in an isolated view in FIG. 5. The plunger 36 includes a base plate 38a and arms 38b that extend from a common side of the base plate 38a. The arms 38b extend, respectively, into the chambers 28 such that each of the flexible bladders 32 is situated between one of the arms 38b and one of the chamber walls 26. In this example, the plunger 36 includes a connector 40 that is attached to an actuator, such a cord 42 (FIGS. 1 and 4). The cord 42 extends through an airtight seal 44 and a side of the container 22. The cord 42 is moveable and, upon movement, serves to move the plunger 36. As will be appreciated, although the plunger 36 is used in this example, the geometry of the plunger 36 may be varied as long as it is moveable and configured to compress and deflate the bladder or bladders 32. In one variation, the plunger 36 may be a piston.

The plunger 36 is moveable, as indicated at arrow M (FIG. 4) between a home position and an upstroke position to compress and thereby deflate the flexible bladders 32 via the vents 34. The compression/deflation changes the volume of the flexible bladders 32. The change in the volume draws a vacuum through the vacuum port 24. In one example, the vacuum pump 20 also includes a bias member 46 (FIG. 4). The bias member 46 biases the plunger 36 toward the home position such that upon actuation to the upstroke position the plunger 36 automatically returns to the home position. The bias member 46 is situated within the container 22, between a side of the container and the plunger 36. In this regard, the container 22, the plunger 36, or both may include features for securing the bias member 46 so that it remains in proper position. Here, the bias member 46 is a coil spring that is mounted on a guide 48 on the plunger 36. As will be appreciated, the bias member 46 may be located elsewhere in the container 22.

FIGS. 6a and 6B illustrate schematic representations of the vacuum pump 20 in, respectively, the home position and the upstroke position. In the home, or rest, position the bladders 32 are fully inflated or expanded. Upon actuation of the cord 42 to move the plunger 36, the arms 38b compress and deflate the bladders 32 (via the vents 34) against the walls 26. That is, the compression of the bladders 32 expels air from the bladders 32 through the vents 34 and thereby changes the volume of the bladders 32. Since the volume inside of the container 22 remains constant, the change in volume of the bladders 32 inside of the container 22 draws a vacuum through the vacuum port 24. The bias member 46 then moves the plunger 36 back to the home position, thereby inflating the bladders 32 through the vents 34. An appropriate check valve may be provided in the vacuum port 24 or in a line that is connected to the vacuum port 24 so that vacuum in the line is not lost.

The vacuum pump 20 is also configured to achieve a relatively high vacuum with minimal displacement of the plunger 36. For example, because the bladders 32 and chambers 28 are elongated in a direction that is approximately perpendicular to the direction of movement of the plunger 36, a small movement of the plunger 36 can displace a relatively large volume of air from the bladders 32. Moreover, use of multiple bladders 32, such as at least three bladders 32, serves to amplify the movement. Such features may be particularly advantageous for pumps used in wearables in which the expansion/contraction of breathing serves as the actuation force for the pump. Such expansion/contraction is typically small, yet the vacuum pump 20 is expected to achieve a relatively high amount of vacuum.

As an example, the displacement and resulting vacuum from that displacement can be represented as a ratio. For instance, the plunger 36 defines a total stroke length L (FIG. 6B), in units of millimeters, from the home position to the upstroke position. The movement from the home position to the upstroke position generates the vacuum, in units of Torr. In one example of the vacuum pump 20, the ratio of the vacuum drawn to the total stroke length is at least 20. In a further example, the stroke length is no greater than about 10 millimeters, and preferably is from 1 to 5 millimeters or even 2 to 4 millimeters.

Figure 8:
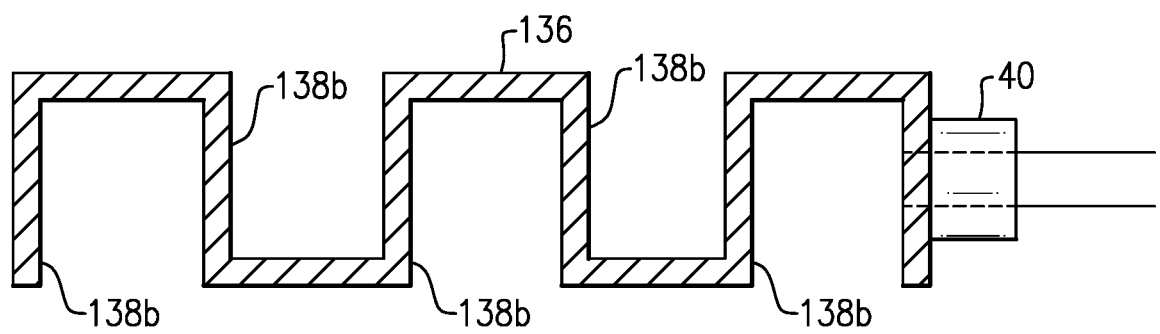
FIG. 8 illustrates an isolated view of a plunger of a vacuum pump.

FIG. 7A illustrates another example of a vacuum pump 120, and FIG. 7B shows a sectioned view. In this disclosure, like reference numerals designate like elements where appropriate and reference numerals with the addition of one-hundred or multiples thereof designate modified elements that are understood to incorporate the same features and benefits of the corresponding elements. In this example, the plunger 136 of the vacuum pump 120 has a serpentine shape. FIG. 8 also shows an isolated view of the plunger 136. Referring also to FIG. 7B, the chamber walls 26 of the container 22 alternate extending from top and bottom of the container 22 rather than all being on one side of the container. The plunger 136 winds above and below the chamber walls 26, with the bladders 32 situated between arms 138b of the plunger 136 and the walls 26. As described above, the plunger deflates the bladders 32 upon movement from the home position to the upstroke position. Bias members 46 return the plunger 136 to the home position. In this example, the airtight seal 44 is located inside of the container 22 rather than on the exterior of the container 22 as in FIG. 4.

Multiple vacuum pumps 20 or 120 can be used in a vacuum pump system. FIGS. 9A and 9B illustrate an example system 80. In this example, the system 80 has multiple vacuum pumps 20, each as described above. As will be appreciated, the system 80 may instead include the pumps 120, or both types of pumps 20 and 120. In the system 80 the pumps 20 are linked together so that they operate in cooperation. For example, the plungers are linked by cords 142, which may be elastic, for co-actuation of the pumps 20. In this example, the pumps 20 are linked in a continuous loop, which may be used as a wearable to utilize the expansion/contraction of breathing as actuation. Upon expansion, the cords 42 move the plungers to generate vacuums as described above for each individual pump 20. Upon contraction, the plungers move to their home positions. Optionally, the system 80 may include an inflatable member 82 located outside of the pumps 20 and to which the pumps (i.e., the pump bodies) are secured. The inflatable member 82 may be a bladder or the like. The inflatable member 82 may serve several functions. For example, the inflatable member 82 may provide anchor points 84 for attachment of one or more of the pumps 20, to thereby secure the pumps 20 in the desired arrangement. The inflatable member 82 may also serve to facilitate capturing the expansion/contraction of breathing movement of the wearer, while also aiding comfort of the wearer. As will be appreciated, the inflatable member 82 may be incorporated into a garment.

Although a combination of features is shown in the illustrated examples, not all of them need to be combined to realize the benefits of various embodiments of this disclosure. In other words, a system designed according to an embodiment of this disclosure will not necessarily include all of the features shown in any one of the Figures or all of the portions schematically shown in the Figures. Moreover, selected features of one example embodiment may be combined with selected features of other example embodiments.

The preceding description is exemplary rather than limiting in nature. Variations and modifications to the disclosed examples may become apparent to those skilled in the art that do not necessarily depart from this disclosure. The scope of legal protection given to this disclosure can only be determined by studying the following claims.

What is claimed is:

1. A pump comprising:
a housing having a port and internal chamber walls, the port opening to an exterior of the housing and the internal chamber walls defining chambers that are in fluid communication with the port;
at least one flexible bladder disposed, respectively, in the chambers, the at least one flexible bladder including a bladder port that opens to the exterior of the housing;
a plunger including arms in the housing that, respectively, extend into the chambers such that the at least one flexible bladder is situated between the arms and the internal chamber walls; and
an actuator connected with the plunger and operable to move the plunger between first and second positions, movement of the plunger from the first to the second position compressing the at least one flexible bladder between the internal chamber walls and the arms and thereby venting the at least one flexible bladder through the bladder port.

2. The pump as recited in claim 1, wherein movement of the plunger from the second to the first position inflates the at least one bladder via the bladder port.

3. The pump as recited in claim 1, further comprising a seal between the actuator and the housing.

4. The pump as recited in claim 3, wherein the seal is convoluted.

5. The pump as recited in claim 1, wherein the actuator is a cord.

6. The pump as recited in claim 1, further comprising a single spring serving as a bias member that biases the plunger toward a home position.

7. The pump as recited in claim 6, wherein the single spring is in the housing sandwiched between a wall of the housing and the plunger.

8. The pump as recited in claim 1, further comprising a check valve connected with the port of the housing.

9. The pump as recited in claim 1, wherein the arms of the plunger are parallel.

10. The pump as recited in claim 1, wherein the arms of the plunger are arranged in a serpentine shape.

11. The pump as recited in claim 1, wherein the chambers are elongated in a direction that is perpendicular to a direction of movement of the plunger between the first and second positions.

12. The pump as recited in claim 1, wherein the at least one flexible bladder includes multiple individual and separate flexible bladders.

13. A pump comprising:
- a housing having a port and internal chamber walls, the port opening to an exterior of the housing and the internal chamber walls defining chambers that are in fluid communication with the port;
- at least one flexible bladder disposed, respectively, in the chambers, the at least one flexible bladder including a bladder port that opens to the exterior of the housing;
- a plunger including arms in the housing that, respectively, extend into the chambers such that the at least one flexible bladder is situated between the arms and the internal chamber walls; and
- an actuator connected with the plunger and operable to move the plunger between second and first positions, movement of the plunger from the second to the first position permitting the at least one flexible bladder to expand between the internal chamber walls and the arms and thereby inflate the at least one bladder via the bladder port.

14. The pump as recited in claim 12, wherein movement of the plunger from the first to the second position compresses the at least one flexible bladder between the internal chamber walls and the arms and thereby vents the at least one flexible bladder through the bladder port.

* * * * *